United States Patent [19]

Baum et al.

[11] Patent Number: 4,556,411

[45] Date of Patent: Dec. 3, 1985

[54] BENZOTHIAZOLE DERIVATIVES FOR PLANT GROWTH AND DEVELOPMENT MODIFICATION

[75] Inventors: Jonathan S. Baum, Pennington; Tsong M. Chen, Princeton Junction, both of N.J.

[73] Assignee: FMC Corporation, Philadelphia, Pa.

[21] Appl. No.: 679,518

[22] Filed: Dec. 7, 1984

[51] Int. Cl.$^4$ .................. A01N 43/78; C07D 417/04; C07D 277/66

[52] U.S. Cl. ........................ 71/90; 544/238; 544/333; 544/405; 546/270; 548/150; 548/178; 548/180

[58] Field of Search ....................... 548/180, 150, 178; 546/280, 270; 544/333, 405, 238; 71/92, 90

[56] References Cited

U.S. PATENT DOCUMENTS 3,876,791  4/1975  Hubbard et al. ..................... 514/367
3,947,582  3/1976  Shen et al. ......................... 514/375
4,319,026  3/1982  Hedrich et al. .................. 548/198 X

FOREIGN PATENT DOCUMENTS

13399W08  1/1973  Japan ................................. 548/180
1090497  11/1967  United Kingdom ................ 548/180

OTHER PUBLICATIONS

Babichev, et al., *Ukr. Khim. Zh.*, 32, 706 (1966).
Bastic, et al., *Glasnik. Hem. Drustva Beograd*, 28, 149 (1963).
Brown, et al., *Pestic. Sci.*, 4, 473 (1973).
Bubnovskaya, et al., *Ukr. Khim. Zh.*, 39, 188 (1973).
Bystrov, et al., *J. Gen. Chem. U.S.S.R.*, 963 (1968).
*Chem. Abstr.*, 51, 373c (1957).
*Chem. Abstr.*, 72, 45003f (1970).
*Chem. Abstr.*, 101, 177262s (1984).
G. F. Katekar, *Phytochem.*, 15, 1421 (1976). Katekar, et al., *Phytochem.*, 20, 2465 (1981).
Katekar, et al., *Plant Physiol.*, 66, 1190 (1980), 60, 826 (1977).

Wada, et al., *J. Med. Chem.*, 16, 930 (1973).

*Primary Examiner*—Richard A. Schwartz
*Attorney, Agent, or Firm*—R. L. Hansen; H. R. Ertelt

[57] ABSTRACT

Benzothiazole compounds of the following structural formula modify the growth and development of plants:

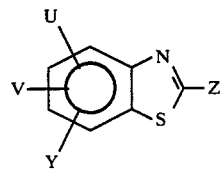

wherein
U is selected from -hydrogen, -halogen, -lower alkyl, -lower haloalkyl, -lower alkoxy, -phenyl, and -phenoxy optionally carrying -halogen and -lower haloalkyl substituents;
V is selected from -hydrogen and -halogen, or U and V taken together are $-C_4H_4-$ joining adjacent ring positions;
Y is selected from -hydrogen and -lower alkoxy;
Z is cyclic and either (a) -phenyl optionally carrying 1 or 2 substituents independently selected from -halogen, -nitro, or two substituents taken together are $-C_4H_4-$ joining adjacent ring positions, or (b) Z may be a saturated or partially unsaturated carbocycle, optionally carrying a bicyclic $-CH_2-$ bridge, or an aromatic heterocycle containing 1 or 2 nitrogen atoms; and
Z includes a 2-oxycarbonyl substituent of the formula

—COOW in which W is selected from -hydrogen, -lower alkyl optionally substituted with -alkoxycarbonyl, and an agriculturally acceptable cation.

27 Claims, No Drawings

BENZOTHIAZOLE DERIVATIVES FOR PLANT GROWTH AND DEVELOPMENT MODIFICATION

This invention is in the field of organic chemical compounds; more specifically, it pertains to novel 2-(oxycarbonylcyclic)benzothiazoles, processes and intermediates thereto, plant growth and development modifying compositions containing 2-(oxycarbonylcyclic)-benzothiazoles, and to the use of 2-(oxycarbonylcyclic)-benzothiazoles for modifying the growth and development of plants.

A number of organic chemical compounds modify the growth and development of plants. Application of an organic chemical to plants may cause death of the plants. Such chemicals are referred to as herbicides. Although broad spectrum herbicides have recognized utility, herbicidal activity is often more desirable if it is selective, sparing crops, but killing weeds. Occasionally organic compounds are discovered which are not simply nutrients, but, when applied in the recommended manner, selectively modify the normal growth and development of plants and do not kill them.

Beneficial effects from such modification include increasing the yield of fruit, seeds, fiber, or other plant products. Another beneficial effect may be an increase in the nutritional value of food products derived from the plants. It is a beneficial effect of some compounds to facilitate harvesting the plant product. Yet another beneficial effect in certain cases is an increase in the products's storage life. Such chemical compounds, beneficial to plants in small amounts, are referred to as plant growth regulators. Plant growth and development modifications leading to such effects include, but are not limited to: root initiation; set, development, ripening and abscission of fruits; plant size and shape; suppression of lodging; control of axillary buds and lateral shoots; metabolism regulation, including senescence; breaking or enforcing dormancy in seeds, buds, and storage organs; promotion or delay of flowering; defoliation; desiccation; and growth promotion under stress.

Sometimes an organic chemical compound displays plant growth and development regulation characterized by both herbicidal activity and plant growth regulator activity depending upon the species of plant, the time of application in the plant growth cycle, the site of application, and the amount of chemical employed, i.e., the application rate.

The plant growth and development modifying 2-(oxycarbonylcyclic)benzothiazoles of this invention are in the latter category. In general, they can be made to behave as either herbicides or plant growth regulators depending upon the way they are used.

An example of a 2-(oxycarbonylcyclic)benzothiazole is 2-(2-carboxyphenyl)benzothiazole, which is a condensed ring heteroaromatic compound of the following structural formula:

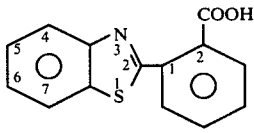

The ring atom numbering scheme is shown for convenient reference. Other 2-(oxycarbonylcarbocyclic)benzothiazoles are numbered in a similar fashion, but in 2-(oxycarbonylheterocyclic)benzothiazoles numbering in the heterocyclic ring conventionally begins with a hetero atom. For the sake of clarity herein, however, the atoms of an oxycarbonylheterocyclic ring in such compounds are numbered beginning with the atom bonded to the benzothiazole moiety, as in the formula which appears above, and this is reflected in the names given the 2-(oxycarbonylcyclic)benzothiazoles of this invention.

Many of the 2-(oxycarbonylcyclic)benzothiazoles within the scope of this invention appear to be new compounds, but others of them have been disclosed. 2-(2-Carboxyphenyl)benzothiazole and the corresponding methyl ester are known; see *Chem. Abstr.*, 51, 373c (1957). In addition, 2-(2-carboxyphenyl)benzothiazoles carrying certain substituents in the carboxylated ring have been described; *Ukranian J. Chem.*, 32, 706 (1966). The latter reference also discloses 2-(carboxypyridinyl)-benzothiazole derivatives.

GB 1,090,497 discloses the herbicidal activity of certain substituted 2-phenylbenzothiazoles. U.S. Pat. No. 4,319,026 describes 2-substituted benzothiazole plant growth regulators.

According to the present invention 2-(2-oxycarbonylcyclic)benzothiazoles of the following formula have been found to modify the growth and development of plants:

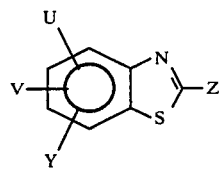

wherein

U is selected from -hydrogen, -halogen, -lower alkyl, -lower haloalkyl, -lower alkoxy, -phenyl, and -phenoxy optionally carrying -halogen and -lower haloalkyl substituents;

V is selected from -hydrogen and -halogen, or U and V taken together are —C$_4$H$_4$— joining adjacent ring positions;

Y is selected from -hydrogen and -lower alkoxy;

Z is cyclic and either (a) -phenyl optionally carrying 1 or 2 substituents independently selected from -halogen, -nitro, or two substituents taken together are —C$_4$H$_4$— joining adjacent ring positions, or (b) Z may be a saturated or partially unsaturated carbocycle, optionally carrying a bicyclic —CH$_2$— bridge, or an aromatic heterocycle containing 1 or 2 nitrogen atoms; and Z includes a 2-oxycarbonyl substituent of the formula

—COOW in which W is selected from -hydrogen, -lower alkyl optionally substituted with -alkoxycarbonyl, and an agriculturally acceptable cation.

In the aforesaid description and wherever employed in this application the terms "halogen" or "halo" mean fluorine, chlorine and bromine. Similarly, the term "lower alkyl" means a straight or branched chain containing 1 to 6, preferably 1 to 4, carbon atoms, and the term "lower alkoxy" contemplates bonded to oxygen a straight or branched chain containing 1 to 6, preferably 1 to 4, carbon atoms. The term "haloalkyl" or the like means one or more hydrogen atoms has been replaced by halogen. "Agriculturally acceptable cation" includes, but is not limited to, alkali and alkaline earth metals such as sodium, potassium, calcium, lithium, and magnesium, or other metals such as copper, zinc, aluminum or iron; ammonium, mono-, di-, or tri-substituted ammonium, such as methylammonium, 1-methylethylammonium, diethylammonium, triethylammonium, hexylammonium, dodecylammonium, ethanolammonium, diethanolammonium, hexanolammonium, or dodecanolammonium.

In addition to the new 2-(2-oxycarbonylcyclic)benzothiazoles as one aspect, the instant invention also includes plant growth and development modifying compositions comprising in admixture with an agriculturally acceptable carrier a plant growth and development modifying effective amount of at least one of the aforesaid 2-(2-oxycarbonylcyclic)benzothiazoles. Furthermore, the invention includes as another aspect the method of modifying the growth and development of plants which comprises applying to the locus where such modification is desired a plant growth and development modifying effective amount of at least one 2-(2-oxycarbonylcyclic)benzothiazole within the aforesaid description.

Among the aforesaid 2-(2-oxycarbonylcyclic)benzothiazoles the most attractive compounds, from the standpoint of plant growth and development modification, are those wherein U is a 5- or 6- substituent selected from -halogen, -lower haloalkyl, -phenyl, and -phenoxy optionally carrying -halogen and -lower haloalkyl substituents. Within this set of compounds it is preferred that V and Y are -hydrogen and that Z is selected from either -phenyl optionally carrying -nitro, or a pyridine ring. As to W, the most active compounds are generally those wherein W is selected from -hydrogen and an agriculturally acceptable cation.

If a 2-(2-oxycarbonylcyclic)benzothiazole is to be used as a herbicide, the most interesting compounds are 2-(2-carboxyphenyl)-5-phenylbenzothiazole, 2-(2-carboxy-3-nitrophenyl)-5-chlorobenzothiazole, 2-(2-carboxyphenyl)-6-(2-chloro-4-trifluoromethylphenoxy)-benzothiazole, and 2-(2-carboxyphenyl)-5-(2-chloro-4-trifluoromethylphenoxy)benzothiazole. Preferred for both preemergence and postemergence application as a herbicide is 2-(2-carboxyphenyl)-6-(2-chloro-4-trifluoromethylphenoxy)benzothiazole.

As plant growth regulators the most attractive properties are displayed by 2-(2-carboxyphenyl)-5-phenylbenzothiazole, 2-(2-carboxyphenyl)-5-trifluoromethylbenzothiazole, 2-(2-carboxyphenyl)-6-phenylbenzothiazole, agriculturally acceptable cation salts of 2-(2-carboxyphenyl)-5-trifluoromethylbenzothiazole, 2-(2-carboxyphenyl)-6-(2-chloro-4-trifluoromethylphenoxy)benzothiazole, 2-(2-carboxyphenyl)-6-phenoxybenzothiazole, 2-(2-carboxy-4-chlorophenyl)-6-phenylbenzothiazole, 2-(2-carboxy-5-chlorophenyl)-6-phenylbenzothiazole, 2-(2-carboxy-4-chlorophenyl)-6-phenoxybenzothiazole, 2-(2-carboxy-5-chlorophenyl)-6-phenoxybenzothiazole, 2-(2-carboxyphenyl)-5-phenoxybenzothiazole, 2-(2-carboxy-6-pyridinyl)-5-phenylbenzothiazole, and 2-(2-carboxyphenyl)-5-(2-chloro-4-trifluoromethylphenoxy)benzothiazole. Among the latter compounds, 2-(2-carboxyphenyl)-5-phenylbenzothiazole, 2-(2-carboxyphenyl)-5-phenoxybenzothiazole, and 2-(2-carboxy-6-pyridinyl)-5-phenylbenzothiazole, especially 2-(2-carboxyphenyl)-5-phenylbenzothiazole, are especially interesting.

The 2-(2-oxycarbonylcyclic)benzothiazoles of this invention can be prepared by adaptations of synthesis techniques described in the literature. The following general technique is employed:

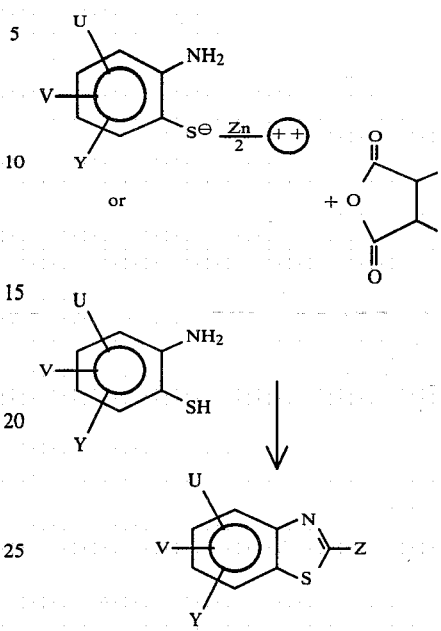

The starting zinc salt can be prepared by the method of Allen and Mackay, *Org. Synth.*, Coll. Vol. II, p.580 (1943). Alternatively, the appropriately substituted o-aminothiophenol can be used. The other reactant is an appropriately substituted phthalic anhydride or carbocyclic or heterocyclic anhydride. These processes will be clarified upon reference to the following Example.

EXAMPLE 1

2-(2-Carboxyphenyl)-5-phenylbenzothiazole

A stirred solution of 0.9 gram (0.006 mole) phthalic anhydride and 1.4 grams (0.003 mole) zinc 2-amino-4-phenylsulfide in 25 mL of acetic acid was heated under reflux for three hours. The reaction mixture was then poured into ice-water and the resultant precipitate collected by filtration. The solid was dried and recrystallized from ethanol. The impure crystalline product was taken up in ethanol and concentrated under reduced pressure to a residual solid. The solid was stirred with aqueous 2N sodium hydroxide and collected by filtration, washed with diethyl ether, then dissolved in 300 mL of water. The resultant solution was combined with the 2N aqueous sodium hydroxide filtrate from above. The combination was filtered, and the filtrate was acidified with concentrated hydrochloric acid. A colorless solid precipitate was collected by filtration. The solid was recrystallized from a mixture of ethanol and water to give 0.6 g 2-(2-carboxyphenyl)-5-phenylbenzothiazole; m.p. 177°–178° C.

The nmr spectrum was consistent with the proposed structure.

Analysis: Calc'd for $C_{20}H_{13}NO_2S$: C 72.48; H 3.95; N 4.23; Found: C 72.72; H 3.77; N 4.20.

Following is a list of other 2-(2-oxycarbonylcyclic)-benzothiazoles within the scope of this invention prepared by similar techniques, together with mp (°C.) where applicable.

EXAMPLE

2: 2-(2-Carboxyphenyl)benzothiazole, mp 186–188.
3: 2-(2-Carboxyphenyl)-5-chlorobenzothiazole, mp 245–250.
4: 2-(2-Carboxyphenyl)-6-chlorobenzothiazole, mp 165–167.
5: 2-(2-Carboxyphenyl)-4,5-dichlorobenzothiozole, mp 242–245.
6: 2-(2-Carboxyphenyl)-4-fluoro-6-chlorobenzothiazole, mp 145–149.
7: 2-(2-Carboxyphenyl)-5-trifluoromethylbenzothiazole, mp 153–155.
8: 2-(2-Carboxyphenyl)-5-methylbenzothiazole, mp 218–220.
9: 2-(2-Carboxyphenyl)-6-methoxybenzothiazole, mp 208–210.
10: 2-(2-Carboxyphenyl)-6-phenylbenzothiazole, mp 181–183.
11: 2-(2-Carboxyphenyl)-naphtho[1,2-d]thiazole, mp 169–170.
12: 2-(2-Carboxy-5-chlorophenyl)benzothiazole, mp 120–125.
13: 2-(2-Carboxy-6-chlorophenyl)benzothiazole monohydrate, mp 149–150.
14: 2-(2-Carboxy-4,5-dichlorophenyl)benzothiazole, mp 125–127.
15: 2-(2-Carboxy-3-nitrophenyl)benzothiazole, mp 230–231.
16: 2-(2-Carboxy-4-nitrophenyl)benzothiazole, mp 234–235.
17: 3-(2-Benzothiazolyl)-2-naphthoic acid, mp 232–233.
18: 2-(2-Carboxy-4-chlorophenyl)-5-chlorobenzothiazole, mp 212–217.
19: 2-(2-Carboxy-6-chlorophenyl)-5-chlorobenzothiazole, monohydrate, mp 223–226, dec.
20: 2-(2-Carboxy-4,5-dichlorophenyl)-5-chlorobenzothiazole, monohydrate, mp 264–267, dec.
21: 2-(2-Carboxy-3-nitrophenyl)-5-chlorobenzothiazole, mp 232.
22: 2-(2-Carboxy-4-nitrophenyl)-5-chlorobenzothiazole, mp 245–246.
23: 3-[2-(5-Chlorobenzothiazolyl)]-2-naphthoic acid, mp 242–243.
24: 2-(2-Carboxyphenylmethyl)-5-chlorobenzothiazole, mp 213–215.
25: 2-(cis-2-Carboxycyclohexyl)benzothiazole, mp 143–144.
2-(2-Carboxy-1-cyclohexyl)benzothiazole, monohydrate, mp 115–116.
27: 2-(cis-2-Carboxy-4-cyclohexyl)benzothiazole, mp 139–140.
28: cis-endo-2-Carboxy-3-benzothiazolylbicyclo[2.2.1]hept-5-ene, mp 175–178.
29: 2-(2-Carboxy-4-pyridinyl)benzothiazole, mp 187–191.
30: 2-(2-Carboxy-6-pyridinyl)benzothiazole, mp 213–215.
31: 2-(2-Carboxy-3-pyrazinyl)benzothiazole, mp 158–160.
32: 2-(cis-2-Carboxycyclohexyl)-5-chlorobenzothiazole, mp 174.
33: 2-(2-Carboxy-4-cyclohexenyl)-5-chlorobenzothiazole, mp 185.
34: cis-endo-2-Carboxy-3-(5-chlorobenzothiazolyl)bicyclo[2.2.1]hept-5-ene, mp 162–165.
35: 2-(2-Carboxy-4-pyridinyl)-5-chlorobenzothiazole, mp 221–225.
36: 2-(2-Carboxy-6-pyridinyl)-5-chlorobenzothiazole, mp 257–260.
37: 2-(2-Carbomethoxyphenyl)benzothiazole, mp 71–72.5.
38: 2-(2-Carbomethoxyphenyl)-5-chlorobenzothiazole, mp 87–90.
39: 2-(2-Carbomethoxy-6-pyridinyl)benzothiazole, mp 112–113.
40: 2-(2-Carboxyphenyl)benzothiazole, 1-methylethylamine salt, mp 110–125.
41: 2-(2-Carboxyphenyl)-5-trifluoromethylbenzothiazole, 1-methylethylamine salt, mp 185–187.
42: 2-(2-Carboxyphenyl)-5-methylbenzothiazole, 1-methylethylamine salt, mp 148–150.
43: 2-(2-Carboxy-4,5-dichlorophenyl)benzothiazole, 1-methylethylamine salt, mp 195–197.
44: 2-(2-Carboxy-3-nitrophenyl)benzothiazole, 1-methylethylamine salt, mp 202–204.
45: 2-(2-Carboxy-4-nitrophenyl)benzothiazole, 1-methylethylamine salt, mp 164–165.
46: 3-(2-Benzothiazoyl)-2-naphthoic acid, 1-methylethylamine salt, mp 173–175.
47: 2-(2-Carboxy-4-chlorophenyl)-5-chlorobenzothiazole, 1-methylethylamine salt.
48: 2-(2-Carboxyphenyl)-6-(2-chloro-4-trifluoromethylphenoxy)benzothiazole, mp 178–180.
49: 2-(2-Carboxyphenyl)-6-chloro-4-phenylbenzothiazole, mp 199–201.
50: 2-(2-Carboxyphenyl)-6-phenoxybenzothiazole, mp 160–161.
51: 2-(2-Carboxy-6-pyridinyl)-6-phenylbenzothiazole, mp 210–212.
52: 2-(2-Carboxy-4-chlorophenyl)-6-phenylbenzothiazole.
53: 2-(2-Carboxy-4-chlorophenyl)-6-phenoxybenzothiazole.
54: 2-(2-Carboxyphenyl)-4,6-dichloro-7-(1-methylethoxy)benzothiazole, mp 210–211.
55: 2-(2-Carboxy-4,5-dichlorophenyl)-6-phenylbenzothiazole, mp 248–249.
56: 2-(2-Carboxy-4-chlorophenyl)-5-phenylbenzothiazole.
57: 2-(2-Carboxyphenyl)-5-phenoxybenzothiazole, mp 154–157.
58: 2-(2-Carboxy-6-pyridinyl)-5-phenylbenzothiazole, mp 194–196.
59: 2-(2-Carboxyphenyl)-4,6-dichloro-7-(1-methylethoxy)benzothiazole, 1-methylethylamine salt, mp 150–152.
60: 2-(2-Carboxymethyl)-5-(2-chloro-4-trifluoromethylphenoxy)benzothiazole, mp 172–175.
61: 2-(2-Carbo-[2-(1-ethoxypropanoyl)oxy]phenyl)benzothiazole, mp 94–96.
62: 2-(2-Carboxy-5-chlorophenyl)-5-chlorobenzothiazole.
63: 2-(2-Carboxy-5-chlorophenyl)-6-phenylbenzothiazole.
64: 2-(2-Carboxy-5-chlorophenyl)-6-phenoxybenzothiazole.
65: 2-(2-Carboxy-5-chlorophenyl)-5-phenylbenzothiazole.

In the normal use of the aforesaid 2-(2-oxycarbonylcyclic)benzothiazole plant growth and development modifiers, the active compounds usually will not be employed free from admixture or dilution, but ordinarily will be used in a suitable formulated agricultural composition compatible with the method of application and comprising a plant growth and development modifying effective amount of at least one of said active compounds. Said benzothiazoles, like most pesticidal agents, may be blended with the agriculturally acceptable surface-active agents and carriers normally employed for facilitating the dispersion of active ingredients, recognizing the accepted fact that the formulation and mode of application of a plant growth and development modifier may affect the activity of the material. The present active compounds may be applied, for example, as sprays, dusts, or granules to the area where plant growth and development modification is desired, the type of application varying of course with the plant and the environment. Thus, the benzothiazole compounds of this invention may be formulated as granules of large particle size, as powdery dusts, as wettable powders, as emulsifiable concentrates, as solutions, and the like.

Granules may comprise porous or nonporous particles, such as attapulgite clay or sand, for example, which serve as carriers for said active compounds. The granule particles are relatively large, a diameter of about 400–2500 microns typically. The particles are either impregnated with the active compound from solution or coated with the compound, adhesive sometimes being employed. Granules generally contain 0.05–20% by weight, preferably 0.5–5%, active ingredient as the plant growth and development modifying effective amount. A typical granular formulation employed for evaluation purposes contains 95% attapulgite clay (24/48 mesh) and 5% 2-(2-carboxyphenyl)-5-phenylbenzothiazole.

Dusts are admixtures of said active compounds with finely divided solids such as talc, attapulgite clay, kieselguhr, pyrophyllite, chalk, diatomaceous earths, calcium phosphates, calcium and magnesium carbonates, sulfur, flours, and other organic and inorganic solids which act as carriers for the plant growth and development modifier. These finely divided solids have an average particle size of less than about 50 microns. A typical dust formulation useful for modifying the growth and development of plants contains by weight 5 parts 2-(2-carboxyphenyl)-5-phenylbenzothiazole and 95 parts talc.

The benzothiazole compounds of the present invention may be made into liquid concentrates by dissolution or emulsification in suitable liquids and into solid concentrates by admixture with talc, clays, and other known solid carriers used in the pesticide art. The concentrates are compositions containing, as a plant growth and development modifying effective amount, about 5–50% the benzothiazole by weight and 95–50% inert material, which includes surface-active dispersing, emulsifying, and wetting agents, but even higher concentrations of active ingredient may be employed experimentally. The concentrates are diluted with water or other liquids for practical application as sprays, or with additional solid carrier for use as dusts. Typical carriers for solid concentrates (also called wettable powders) include fuller's earth, clays, silicas, and other highly absorbent, readily wetted inorganic diluents.

Manufacturing concentrates are useful for shipping low melting products of this invention. Such concentrates are prepared by melting the solid products together with one percent or more of a solvent to produce a concentrate which does not solidify on cooling to the freezing point of the pure product or below.

Useful liquid concentrates include the emulsifiable concentrates, which are homogeneous liquid or paste compositions readily dispersed in water or other liquid carriers. They may consist entirely of the active compound with a liquid or solid emulsifying agent, or they may also contain a liquid carrier such as xylene, heavy aromatic naphthas, isophorone and other relatively non-volatile organic solvents. For application, these concentrates are dispersed in water or other liquid carriers and normally applied as sprays to areas to be treated.

Typical surface-active wetting, dispersing, and emulsifying agents used in agricultural formulations include, for example, the alkyl and alkylaryl sulfonates and sulfates and their sodium salts; alkylamide sulfonates, including fatty methyl taurides; alkylaryl polyether alcohols, sulfated higher alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises about 1–15% by weight of the plant growth regulator composition.

Other useful formulations include simple solutions of the active ingredient in a solvent in which it is completely soluble at the desired concentration, such as acetone or other organic solvents.

A plant growth and development modifying effective amount of said benzothiazole in a plant growth and development modifying composition diluted for application is normally in the range of about 0.004% to about 5% by weight. Many variations of spraying and dusting compositions known in the art may be used by substituting said plant growth and development modifying compounds of this invention into compositions known or apparent to the art. The plant growth and development modifying compositions of this invention may be formulated with other active ingredients, including insecticides, nematicides, acaricides, fungicides, other herbicides or plant growth regulators, fertilizers, etc.

In using the compositions to modify plant growth and development according to the method of this invention, it is only necessary that a plant growth and development modifying, or herbicidally, or plant growth regulant, effective amount of at least one of said benzothiazoles, depending on the objective, be applied to the locus where such modification, or control, or regulation is desired, generally a soil locus where agricultural crops are grown and either before or, preferably, after the plants have emerged. Liquid plant growth regulator compositions may be incorporated into the soil, applied to the soil as a drench, or sprayed on the foliage of growing plants. Solid compositions may be applied by broadcasting or in bands. For most applications, a plant growth and development modifying, or herbicidally, or plant growth regulant, effective amount will be about 0.005 to 8 kg, preferably 0.01 to 2 kg, per hectare.

The plant growth and development modifiers of this invention were investigated for activity in preemergence and postemergence tests according to the following procedure:

Flats were filled with a steam-sterilized sandy loam soil. Seeds of the following test plant species were planted in furrows: cotton (*Gossypium hirsutum*) or limabean (*Phaseolus limensis*), field corn (*Zea mays L.*), soybean (*Glycine max*), wheat (*Triticum aestivum*), barnyardgrass (*Echinochload crus galli*), johnsongrass (*Sorghum halepense*), pitted morningglory (*Ipomoea lacunosa*), velvetleaf (*Abutilon theophrasti*), field bindweed (*Convolvulus arvenia*), and green foxtail (*Setaria viridis*). Soil was leveled to a 1 cm depth over the seeds.

In both the preemergence and postemergence tests the test chemicals were applied as aqueous acetone solutions at a rate equivalent to 8.0 kilograms/hectare.

A flat for preemergence test was watered and the soil evenly drenched with the water-acetone solution of test chemical. The treated flat was placed in a greenhouse where it was watered regularly at the soil surface for a period of 13 days. The effect of the test chemical was then recorded. In some tests individual plant species were examined for percent kill and a vigor rating of one to five was assigned to the surviving plants, a vigor of five signifying no chemical injury. In other tests percent kill and vigor rating were combined in a single rating called "percent control," which has the following significance:

| Percent Control | Description of Effect | Effect on Crops | Effect on Weeds |
|---|---|---|---|
| 0 | No effect | No crop reduction | No weed control |
| 10 |  | Slight discoloration or stunting | Very poor weed control |
| 20 | Slight effect | Some discoloration, stunting or stand loss | Poor weed control |
| 30 |  | Crop injury more pronounced but not lasting | Poor to deficient weed control |
| 40 |  | Moderate injury, crop usually recovers | Deficient weed control |
| 50 | Moderate effect | Crop injury more lasting, recovery | Deficient to moderate weed control |
| 60 |  | Lasting crop injury no recovery | Moderate weed control |
| 70 |  | Heavy injury and stand loss | Control somewhat less than satisfactory |
| 80 | Severe effect | Crop nearly destroyed a few survivors | Satisfactory to good weed control |
| 90 |  | Only occasional live plants left | Very good to excellent control |
| 100 | Completely effective | Complete crop destruction | Complete weed destruction |

Footnotes denoting other morphological responses observed were also recorded.

A flat for postemergence test was placed in a greenhouse for an 8 to 10 day growing period. The test solution was then hand-sprayed onto the foliage of the emerged test plants. After spraying, the foliage of the test plants was kept dry for 24 hours after which time regular watering was resumed for a period of 13 days. The effect of the test chemical was then recorded in the same manner described for the preemergence tests.

The results of the preemergence and postemergence tests appear in Tables I and II, respectively. In the Tables, columns headed "PC," "V," "K," and "F" refer to percent control, vigor, kill, and footnotes, respectively.

Footnotes B, C, D, E, G, H, J, M, P, Q, and U, defined in the Tables and described in more detail below, indicate plant growth regulator activity.

Stunting (footnote B) can retard the growth of grasses, which reduces maintenance time for lawns, golf courses, and highway rights-of-way. Stunting in fruit trees may reduce stem growth, which can reduce pruning and trimming time. Stunting in cereal and broadleaf crops such as wheat, cotton, and soybeans may result in a shorter, thicker stalk which resists lodging, in turn promoting higher yields.

Desiccation (footnote C) can reduce the pre-harvest moisture content in cereals such as wheat, or in broadleaf crops such as sunflower. Desiccation can result in the loss of foliage, and in such plants as soybeans, cotton, peanuts, and potatoes the loss of foliage aids in harvesting.

Axillary growth stimulation (footnote D), or branching, can lead to multiple stems in cereals such as wheat (tillering). An increase in the number of stems may increase the yield. In soybeans, axillary stimulation at flowering can result in more fruits, increasing yield.

Nastic response (footnote E) is manifested by twisting the bending of the plants and indicates a hormonal disruption. A natural and useful nastic response is the curling of a tendril or stem around a support, e.g., in peas and pole beans.

Stimulation (footnote G) of vegetative growth in crops such as clover results in increased yields of forage. The stimulation of reproductive growth in fruits and cereals will also result in increased yields from those crops.

Defoliation (footnote H), or loss of plant foliage just prior to harvesting crops such as soybeans, cotton, peanuts and potatoes will facilitate harvest of those crops. Foliage present at the time cotton is harvested may stain the cotton.

Intumescence (footnote J) indicates formation of abnormal swellings, a disruption of the hormonal balance that promotes normal growth. Intumescence-causing agents can promote the growth of tissue, such as tobacco callus.

Negative root geotropism (footnote M) connotes the upward growth of roots out of the soil and indicates disruption of the plant's normal hormonal balance. There can be a correlation between negative root geotropism and increase in the number of pods on soybean plants.

Deeper green lower leaves (footnote P) suggests delay of senescence, increased chlorophyll production, or chlorophyll retention. These phenomena mean greater photosynthesis, which may increase yield from plants such as soybeans.

Leaf alteration (footnote Q) indicates disruption in the plant's hormonal balance. Leaves of plants can be altered to allow better utilization of sunlight, which may enhance plant growth.

Benzothiazoles of this invention were also found in separate tests to inhibit the transport of auxin in excised stems of soybean plants, to affect geotropic response in cress (*Lepidium sativum*) seedlings, and to enhance pod set in soybean plants.

TABLE I

Preemergence Tests Plant

| Example | Barngr V | Barngr PC or K | Barngr F | Bindweed V | Bindweed PC or K | Bindweed F | Corn-F V | Corn-F PC or K | Corn-F F | Greenfox V | Greenfox PC or K | Greenfox F | Mrnglory V | Mrnglory PC or K | Mrnglory F | Johngr V | Johngr PC or K | Johngr F | Cotton¹ Lima Bean V | Cotton¹ Lima Bean PC or K | Cotton¹ Lima Bean F | Soybean V | Soybean PC or K | Soybean F | Velvetlf V | Velvetlf PC or K | Velvetlf F | Wheat V | Wheat PC or K | Wheat F |
|---|---|---|---|---|---|---|---|---|---|---|---|---|---|---|---|---|---|---|---|---|---|---|---|---|---|---|---|---|---|---|
| 1 | 2 | 90 | BA | 3 | 50 | EB | 0 | 100 | 0 | 2 | 50 | EB | | 0 | EB | 2 | 85 | B | 0 | 100 | B | 2 | 50 | BA | 3 | 0 | EB | 2 | 85 | B |
| 2 | 5 | 0 | B | 5 | 0 | 0 | 4 | 30 | 0 | 5 | 0 | 0 | 5 | 0 | 0 | 5 | 0 | 0 | 4 | 40 | BK | 4 | 80 | BK | 5 | 0 | 0 | 4 | 0 | BE |
| 3 | 4 | 0 | 0 | 4 | 0 | B | 4 | 0 | 0 | 4 | 0 | B | 3 | 0 | E | 4 | 0 | 0 | 5 | 0 | 0 | 4 | 0 | 0 | 4 | 60 | B | 5 | 0 | 0 |
| 4 | 3 | 0 | BE | 4 | 0 | E | 4 | 0 | M | 4 | 0 | B | 4 | 60 | BE | 4 | 0 | BE | 5 | 0 | BE | 4 | 0 | 0 | 4 | 0 | 0 | 4 | 0 | E |
| 5 | 4 | 0 | B | 4 | 70 | BE | 4 | 0 | B | 4 | 0 | B | 4 | 10 | E | 4 | 0 | B | 2 | 0 | 0 | 4 | 0 | 0 | 4 | 20 | BE | 5 | 0 | 0 |
| 6 | 4 | 0 | MP | 5 | 20 | A | 5 | 30 | AI | 4 | 0 | M | 5 | 0 | 0 | 5 | 0 | 0 | 4 | 0 | 0 | 3 | 50 | BM | 4 | 70 | B | 4 | 0 | A |
| 7 | 4 | 0 | M | 4 | 0 | 0 | 4 | 0 | AM | 4 | 0 | M | 5 | 0 | 0 | 5 | 0 | 0 | 5 | 0 | 0 | 5 | 20 | ABI | 5 | 0 | 0 | 4 | 0 | AM |
| 8 | 5 | 0 | 0 | 4 | 0 | B | 5 | 0 | 0 | 4 | 0 | 0 | 4 | 0 | 0 | 5 | 0 | 0 | 4 | 0 | 0 | 5 | 0 | B | 4 | 0 | 0 | 4 | 0 | B |
| 9 | 5 | 0 | 0 | 5 | 0 | 0 | 5 | 0 | 0 | 5 | 0 | 0 | 5 | 0 | 0 | 5 | 0 | 0 | 5 | 0 | 0 | 3 | 0 | B2E | 4 | 0 | 0 | 4 | 0 | AE |
| 10 | 10 | 0 | ABI | 20 | 0 | ABI | 30 | 0 | AK | 40 | 0 | AB2E | 0 | 0 | 0 | 10 | 0 | ABI | 20 | 0 | ABI | 50 | 0 | B2E | 10 | 0 | 0 | 10 | 0 | BE |
| 11 | 4 | 0 | BE | 5 | 0 | 0 | 4 | 0 | 0 | 4 | 0 | B | 4 | 0 | A | 5 | 0 | 0 | 0 | 100 | K | 4 | 30 | B | 4 | 0 | 0 | 4 | 0 | A |
| 12 | 4 | 0 | A | 4 | 20 | B | 4 | 0 | 0 | 4 | 0 | A | 4 | 10 | AB | 3 | 0 | 90 B | 4 | 0 | A | 3 | 50 | B | 5 | 100 | 0 | 5 | 0 | 0 |
| 13 | 5 | 0 | 0 | 5 | 0 | 0 | 5 | 0 | 0 | 5 | 0 | 0 | 4 | 50 | AB | 5 | 0 | 0 | 5 | 0 | 0 | 4 | 10 | BM | 4 | 10 | A | 4 | 0 | A |
| 14 | 5 | 0 | 0 | 4 | 0 | 0 | 5 | 100 | 0 | 5 | 0 | 0 | 4 | 0 | BE | 5 | 0 | 0 | 5 | 0 | 0 | 3 | 95 | AM | 5 | 35 | AB | 5 | 0 | 0 |
| 15 | 5 | 0 | 0 | 4 | 0 | BE | 5 | 0 | 0 | 5 | 0 | 0 | 5 | 0 | 0 | 5 | 0 | 0 | 5 | 0 | 0 | 4 | 0 | 0 | 4 | 0 | 3 | 4 | 0 | A |
| 16 | 5 | 0 | 0 | 5 | 0 | 0 | 5 | 0 | 0 | 4 | 40 | AB | 5 | 30 | B | 5 | 0 | 0 | 5 | 0 | 0 | 4 | 0 | B | 4 | 50 | B | 5 | 0 | 0 |
| 17 | 5 | 0 | A | 4 | 80 | 0 | 5 | 0 | 0 | 4 | 70 | 0 | 5 | 50 | B | 4 | 0 | 0 | 5 | 0 | 0 | 5 | 50 | B | 5 | 0 | A | 5 | 0 | 0 |
| 18 | 4 | 0 | B | 5 | 0 | 0 | 4 | 0 | 0 | 5 | 0 | 0 | 4 | 0 | 0 | 5 | 0 | 0 | 5 | 0 | 0 | 4 | 30 | 0 | 4 | 0 | 0 | 4 | 0 | A |
| 19 | 4 | 0 | A | 5 | 0 | 0 | 5 | 0 | 0 | 5 | 0 | A | 5 | 0 | 0 | 5 | 0 | 0 | 5 | 0 | 0 | 5 | 0 | A | 4 | 0 | 0 | 5 | 0 | A |
| 20 | 5 | 0 | 0 | 5 | 0 | 0 | 5 | 0 | M | 5 | 0 | 0 | 4 | 0 | EK | 5 | 0 | 0 | 5 | 0 | 0 | 4 | 30 | K | 4 | 0 | E | 4 | 0 | 0 |
| 21 | 5 | 0 | 0 | 5 | 0 | E | 5 | 0 | 0 | 5 | 0 | 0 | 4 | 0 | 0 | 5 | 0 | 0 | 5 | 0 | 0 | 5 | 0 | A | 5 | 0 | 0 | 5 | 0 | A |
| 22 | 5 | 0 | A | 4 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | A | 5 | 0 | 0 |
| 23 | 5 | 0 | 0 | 5 | 0 | C | 5 | 0 | 0 | 5 | 0 | 0 | 5 | 0 | 0 | 5 | 0 | 0 | 5 | 0 | 0 | 5 | 0 | 0 | 5 | 3 | AB | 5 | 0 | A |
| 24 | 5 | 0 | 0 | 5 | 10 | B | 5 | 0 | 0 | 5 | 0 | 0 | 5 | 0 | A | 5 | 0 | 0 | 5 | 0 | 0 | 4 | 0 | A | 5 | 0 | 0 | 5 | 0 | 0 |
| 25 | 5 | 0 | 0 | 4 | 0 | 0 | 5 | 0 | 0 | 2 | 40 | AB | 5 | 0 | 0 | 5 | 0 | 0 | 5 | 60 | 0 | 5 | 0 | 0 | 5 | 10 | AB | 5 | 0 | 0 |
| 26 | 5 | 0 | 0 | 5 | 0 | 0 | 5 | 0 | 0 | 4 | 70 | B | 4 | 30 | B | 5 | 0 | 0 | 5 | 0 | BM | 4 | 0 | BM | 4 | 80 | B | 5 | 0 | 0 |
| 27 | 5 | 0 | 0 | 5 | 0 | BE | 5 | 0 | 0 | 5 | 0 | 0 | 4 | 50 | B | 5 | 0 | 0 | 5 | 0 | 0 | 5 | 0 | 0 | 5 | 0 | 0 | 5 | 0 | A |
| 28 | 5 | 0 | ABE | 4 | 0 | BE | 4 | 0 | A | 5 | 0 | 0 | 4 | 20 | ABE | 5 | 0 | 0 | 4 | 0 | 0 | 4 | 0 | AI | 4 | 0 | BE | 4 | 0 | ABE |
| 29 | 4 | 0 | E | 5 | 0 | BE | 4 | 0 | B | 5 | 0 | 0 | 4 | 20 | BEM | 4 | 40 | B | 4 | 60 | 0 | 3 | 20 | BDI | 3 | 60 | B | 4 | 0 | EM |
| 30 | 4 | 0 | 0 | 3 | 0 | 0 | 4 | 0 | BIM | 5 | 0 | 0 | 5 | 0 | 0 | 4 | 0 | 0 | 4 | 0 | 0 | 4 | 0 | BE | 4 | 0 | BE | 4 | 0 | B |
| 31 | 4 | 0 | 0 | 5 | 0 | 0 | 4 | 0 | 0 | 5 | 0 | 0 | 4 | 0 | 0 | 4 | 0 | 0 | 4 | 0 | 0 | 4 | 0 | BD | 4 | 0 | 0 | 5 | 0 | 0 |
| 32 | 4 | 0 | 0 | 5 | 0 | BE | 5 | 0 | 0 | 5 | 0 | 0 | 5 | 0 | 0 | 5 | 0 | 0 | 4 | 60 | 0 | 4 | 20 | B | 4 | 0 | 0 | 5 | 0 | 0 |
| 33 | 4 | 0 | ABE | 3 | 70 | BE | 4 | 0 | 0 | 5 | 0 | 0 | 5 | 0 | 0 | 5 | 0 | 0 | 5 | 0 | BE | 5 | 70 | BE | 5 | 50 | BE | 5 | 0 | AE |
| 34 | 5 | 0 | BE | 5 | 30 | BE | 5 | 0 | 0 | 5 | 0 | 0 | 3 | 30 | BE | 4 | 0 | BE | 3 | 40 | BE | 3 | 60 | B | 3 | 40 | BE | 5 | 0 | BE |
| 35 | 4 | 0 | 0 | 5 | 0 | 0 | 5 | 0 | 0 | 5 | 0 | 0 | 5 | 0 | 0 | 5 | 0 | 0 | 5 | 0 | 0 | 4 | 0 | 0 | 4 | 0 | 0 | 4 | 0 | 0 |
| 36 | 5 | 0 | 0 | 4 | 0 | B | 4 | 0 | M | 4 | 0 | 0 | 4 | 0 | M | 4 | 0 | M | 4 | 0 | M | 4 | 0 | M | 4 | 0 | 0 | 4 | 0 | M |
| 37 | 4 | 0 | M | 4 | 0 | AB | 4 | 0 | M | 4 | 30 | A | 4 | 0 | ABM | 4 | 0 | BM | 3 | 40 | M | 4 | 0 | BM | 5 | 0 | BM | 4 | 0 | M |
| 38 | 5 | 0 | ABMP | 5 | 0 | 0 | 4 | 0 | ABM | 5 | 0 | 0 | 3 | 60 | A | 4 | 0 | BM | 3 | 80 | ABIM | 3 | 30 | ABIM | 4 | 0 | AB | 4 | 0 | AM |
| 39 | 4 | 0 | AMP | 5 | 10 | AB | 5 | 0 | AM | 5 | 0 | BM | 3 | 30 | AB | 4 | 0 | AB | 4 | 0 | AIM | 4 | 0 | BM | 5 | 0 | 0 | 4 | 0 | AM |
| 40 | 4 | 0 | 0 | 5 | 0 | 0 | 4 | 0 | 0 | 5 | 0 | 0 | 4 | 0 | 0 | 5 | 0 | 0 | 5 | 0 | 0 | 5 | 10 | M | 4 | 0 | 0 | 5 | 0 | 0 |
| 41 | 5 | 0 | 0 | 4 | 30 | 0 | 5 | 0 | 0 | 4 | 0 | 0 | 5 | 0 | 0 | 5 | 0 | 0 | 5 | 0 | 0 | 5 | 0 | 0 | 4 | 60 | BM | 5 | 0 | 0 |
| 42 | 5 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | 0 | 4 | 80 | AB | 5 | 0 | 0 |
| 48 | 80 | B4AEI | | 100 | 0 | | 10 | B1 | | 100 | 0 | | 90 | B4AE | | 80 | B5EA | | 50 | B2AIE | | 20 | B2E | | 100 | 0 | | 10 | B1E | |

TABLE I-continued

Preemergence Tests Plant

| Example | Barngr V | Barngr K or F | Bindweed V | Bindweed K or F | Corn-F V | Corn-F K or F | Greenfox V | Greenfox K or F | Mrnglory V | Mrnglory K or F | Johngr V | Johngr K or F | Cotton¹ Lima Bean V | Cotton¹ Lima Bean K or F | Soybean V | Soybean K or F | Velvetlf V | Velvetlf K or F | Wheat V | Wheat K or F |
|---|---|---|---|---|---|---|---|---|---|---|---|---|---|---|---|---|---|---|---|---|
| 49 | 10 | AB1M | 0 | 0 | 30 | AB3 | 20 | AB2 | 0 | 0 | 10 | AB1M | 30 | AB1 | 50 | B2 | 20 | B1 | 0 | 0 |
| 50 | 60 | AB3E | 60 | BE | 80 | B3E | 60 | B5E | 40 | BE | 60 | AB3E | 40 | B3 | 60 | B3 | 30 | BEI | 40 | AB1E |
| 51 | 0 | 0 | 0 | 0 | 10 | M | 0 | 0 | 0 | 0 | 0 | 0 | 0 | 0¹ | 10 | M | 0 | 0 | 40 | E |
| 54 | 0 | M | 0 | 0 | 30 | B2M | 0 | 0 | 0 | M | 0 | 0 | 0 | M¹ | 0 | K | 0 | 0 | 0 | 0 |
| 55 | 0 | 0 | 0 | 0 | 0 | 0 | 0 | 0 | 0 | 0 | 0 | 0 | 0 | 0 | 0 | 0 | 0 | 0 | 0 | 0 |
| 57 | 0 | 0 | 80 | BE | 30 | B3MP | 20 | E | 40 | BE | 10 | M | 60 | B3M¹ | 50 | B3M | 70 | B | 80 | EB3 |
| 58 | 50 | B3E | 80 | BE | 50 | B3PE | 0 | 0 | 80 | BE | 40 | B2E | 80 | B5E¹ | 70 | B5E | 80 | BE | 50 | EB2 |
| 59 | 0 | 0 | 20 | B2A | 40 | B2M | 20 | B2AI | 20 | B2AI | 20 | B2 | 0 | 0¹ | 0 | 0 | 40 | B2AI | 0 | 0 |
| 60 | 0 | 0 | 0 | 0 | 0 | 0 | 0 | 0 | 0 | 0 | 0 | 0 | 0 | 0 | 0 | 0 | 0 | 0 | 0 | 0 |
| 61 | 0 | 0 | 10 | AB1 | 20 | AB1 | 0 | M | 10 | AB1M | 10 | AB1M | 10 | AB3 | 10 | B2 | 10 | B1 | 0 | 0 |

FOOTNOTES
V = Vigor
5 = Plants normal
4 = Slight injury; plants will or have already recovered
3 = Moderate injury; plants expected to recover
2 = Moderate to severe injury; plants are not expected to recover
1 = Severe injury; plants will not recover
0 = Dead plant
K = % Kill
F = Footnote:
A = Necrosis
B = Stunted
C = Desiccation
D = Axillary Growth Stimulation
E = Nastic Responses
F = Necrotic Spots
G = Growth Stimulation
H = Defoliant
I = Chlorosis
J = Intumescence
K = Suspected germination failure
L = Stand may be affected by non-chemical factors
M = Negative root geotropism
N = Bleaching
P = Deeper green lower leaves
Q = Leaf alterations
U = Any other morphological response
Sub-footnotes:
1 = 0%–4%
2 = 25%–49%
3 = 50%–74%
4 = 75%–100%
5 = refers to stunting only 75%–100% stunted with 0–30% phytotoxicity
¹Data for cotton

TABLE II

Postemergence Tests
Plant

| Example | Barngr PC or V | K | F | Bindweed PC or V | K | F | Corn-F PC or V | K | F | Greenfox PC or V | K | F | Mrnglory PC or V | K | F | Johngr PC or V | K | F | Cotton[1] Lima Bean PC or V | K | F | Soybean PC or V | K | F | Velvetlf PC or V | K | F | Wheat PC or V | K | F |
|---|---|---|---|---|---|---|---|---|---|---|---|---|---|---|---|---|---|---|---|---|---|---|---|---|---|---|---|---|---|---|
| 1 | 4 | 0 | BCM | 4 | 0 | BEM | 4 | 0 | M | 4 | 0 | BCM | 4 | 0 | BEM | 4 | 0 | M | 3 | 0 | EBM | 3 | 0 | EBCM | 4 | 0 | BEM | 4 | 0 | BM |
| 2 | 5 | 0 | 0 | 5 | 0 | 0 | 5 | 0 | 0 | 4 | 0 | A | | | | | | | 4 | 0 | A | 4 | 0 | AD | 5 | 0 | 0 | 5 | 0 | 0 |
| 3 | 4 | 0 | A | 5 | 0 | 0 | 5 | 0 | 0 | 4 | 0 | B | 5 | 0 | 0 | 5 | 0 | 0 | 5 | 0 | 0 | 5 | 0 | 0 | 5 | 0 | 0 | 4 | 0 | A |
| 4 | 4 | 0 | AB | 3 | 95 | B | 5 | 0 | 0 | 4 | 70 | 0 | 4 | 0 | 0 | 4 | 0 | B | 3 | 0 | ABE | 4 | 0 | AD | 2 | 90 | AB | 5 | 0 | 0 |
| 5 | 5 | 0 | 0 | 4 | 0 | BE | 5 | 0 | 0 | 5 | 0 | 0 | 5 | 0 | 0 | 5 | 0 | 0 | 4 | 0 | AB | 4 | 0 | AD | 4 | 0 | E | 5 | 0 | 0 |
| 7 | 4 | 0 | C | 3 | 0 | CE | 4 | 0 | C | 3 | 0 | BC | 4 | 0 | C | 4 | 0 | C | 3 | 0 | BDI | 4 | 0 | DI | 3 | 0 | CE | 4 | 0 | C |
| 8 | 4 | 0 | C | 4 | 20 | C | 4 | 0 | C | 4 | 0 | C | 4 | 0 | C | 4 | 0 | C | 4 | 0 | C | 4 | 0 | CD | 4 | 0 | C | 4 | 0 | C |
| 9 | 5 | 0 | 0 | 5 | 0 | 0 | 5 | 0 | 0 | 5 | 0 | 0 | 5 | 0 | 0 | 5 | 0 | 0 | 5 | 0 | 0 | 4 | 0 | A | 5 | 0 | 0 | 5 | 0 | 0 |
| 10 | | | | 0 | | 0 | 30 | | MB2EC1 | 0 | | 0 | 10 | | EC1 | 40 | | B2C1 | 10 | | H2 | 50 | | EB5PDM | 10 | | EC1 | 0 | | 0 |
| 11 | 4 | 0 | C | 5 | 0 | 0 | 5 | 0 | 0 | 5 | 0 | 0 | 5 | 0 | 0 | 5 | 0 | 0 | 4 | 0 | C | 4 | 0 | | 5 | 0 | 0 | 5 | 0 | 0 |
| 12 | 5 | 0 | 0 | 3 | 70 | BCM | 5 | 0 | 0 | 4 | 0 | M | 3 | 0 | BM | 5 | 0 | 0 | 3 | 0 | CD | 4 | 0 | CD | 4 | 0 | CM | 5 | 0 | 0 |
| 13 | 5 | 0 | 0 | 5 | 0 | 0 | 5 | 0 | 0 | 5 | 0 | 0 | 5 | 0 | 0 | 5 | 0 | 0 | 4 | 0 | C | 4 | 0 | C | 5 | 0 | 0 | 5 | 0 | 0 |
| 14 | 5 | 0 | 0 | 5 | 0 | 0 | 5 | 0 | 0 | 4 | 20 | 0 | 5 | 0 | 0 | 5 | 0 | 0 | 4 | 0 | C | 5 | 0 | 0 | 5 | 0 | 0 | 5 | 0 | 0 |
| 15 | 5 | 0 | 0 | 4 | 90 | BL | 5 | 0 | 0 | 4 | 90 | BC | 4 | 0 | BC | 5 | 0 | 0 | 4 | 0 | BCD | 4 | 0 | BCD | 3 | 70 | BC | 5 | 0 | 0 |
| 16 | 5 | 0 | 0 | 3 | 0 | C | 5 | 0 | 0 | 5 | 0 | 0 | 5 | 0 | 0 | 5 | 0 | 0 | 4 | 0 | CD | 4 | 0 | C | 5 | 0 | 0 | 5 | 0 | 0 |
| 17 | 5 | 0 | 0 | 4 | 50 | B | 4 | 0 | BC | 5 | 0 | 0 | | | | 5 | 0 | 0 | 4 | 0 | C | 4 | 0 | BC | 4 | 20 | B | 5 | 0 | 0 |
| 18 | 5 | 0 | 0 | 2 | 95 | BC | 5 | 0 | 0 | 4 | 30 | C | 4 | 0 | BC | 5 | 0 | 0 | 4 | 0 | C | 4 | 0 | CD | 4 | 0 | B | 5 | 0 | 0 |
| 19 | 5 | 0 | 0 | 5 | 0 | 0 | 5 | 0 | 0 | 5 | 0 | 0 | 5 | 0 | 0 | 5 | 0 | 0 | 4 | 0 | A | 5 | 0 | 0 | 5 | 0 | 0 | 5 | 0 | 0 |
| 20 | 5 | 0 | 0 | 5 | 0 | 0 | 5 | 0 | 0 | 5 | 0 | 0 | 5 | 0 | 0 | 5 | 0 | 0 | 4 | 0 | A | 4 | 0 | A | 5 | 0 | 0 | 5 | 0 | 0 |
| 21 | 5 | 0 | 0 | 0 | 100 | L | 5 | 0 | 0 | 4 | 90 | C | 3 | 70 | BC | 5 | 0 | 0 | 4 | 0 | BC | 3 | 0 | BCD | 4 | 0 | BC | 5 | 0 | 0 |
| 22 | 5 | 0 | 0 | 2 | 30 | BC | 5 | 0 | 0 | 4 | 0 | C | 5 | 0 | 0 | 5 | 0 | 0 | 4 | 0 | C | 5 | 0 | 0 | 5 | 0 | 0 | 5 | 0 | 0 |
| 23 | 5 | 0 | 0 | 5 | 0 | 0 | 5 | 0 | 0 | 5 | 0 | 0 | 5 | 0 | 0 | 5 | 0 | 0 | 4 | 0 | CD | 4 | 0 | C | 5 | 0 | 0 | 4 | 0 | I |
| 24 | 4 | 0 | A | 5 | 0 | 0 | 5 | 0 | 0 | 5 | 0 | 0 | 4 | 0 | A | 4 | 30 | A | 5 | 0 | 0 | 5 | 0 | 0 | 4 | 20 | A | 2 | 10 | A |
| 25 | 4 | 0 | A | 5 | 0 | 0 | 4 | 0 | A | 5 | 0 | 0 | 4 | 0 | A | 5 | 0 | 0 | 4 | 0 | AD | 4 | 0 | A | 5 | 0 | 0 | 4 | 0 | A |
| 26 | 4 | 0 | C | 4 | 30 | C | 4 | 0 | BCM | 5 | 0 | 0 | 4 | 0 | BC | 5 | 0 | 0 | 4 | 0 | CIM | 4 | 0 | CDIM | 5 | 0 | 0 | 4 | 0 | CM |
| 27 | 5 | 0 | 0 | 5 | 0 | 0 | 4 | 0 | C | 4 | 0 | AI | 5 | 0 | 0 | 5 | 0 | 0 | 4 | 0 | CD | 4 | 0 | CD | 5 | 0 | 0 | 5 | 0 | 0 |
| 28 | 5 | 0 | 0 | 5 | 0 | 0 | 5 | 0 | 0 | 3 | 20 | A | 5 | 0 | 0 | 4 | 0 | I | 4 | 0 | AB | 4 | 0 | A | 5 | 0 | 0 | 4 | 0 | I |
| 29 | 5 | 0 | 0 | 4 | 0 | BE | 5 | 0 | 0 | 5 | 0 | 0 | 5 | 0 | 0 | 5 | 0 | 0 | 3 | 0 | ABD | 4 | 0 | ABDI | 5 | 0 | 0 | 5 | 0 | 0 |
| 30 | 5 | 0 | 0 | 4 | 0 | E | 5 | 0 | 0 | 5 | 0 | 0 | 5 | 0 | 0 | 5 | 0 | 0 | 4 | 0 | E | 4 | 0 | E | 4 | 0 | E | 5 | 0 | 0 |
| 31 | 5 | 0 | 0 | 4 | 0 | ABE | 5 | 0 | 0 | 4 | 0 | A | 5 | 0 | 0 | 5 | 0 | 0 | 4 | 0 | CB | 4 | 0 | BCD | 4 | 0 | 0 | 5 | 0 | 0 |
| 32 | 4 | 0 | C | 4 | 0 | C | 4 | 0 | BC | 4 | 0 | C | 4 | 0 | C | 4 | 0 | C | 4 | 0 | CB | 4 | 0 | BC | 4 | 0 | C | 4 | 0 | C |
| 33 | 5 | 0 | 0 | 5 | 0 | 0 | 5 | 0 | 0 | 5 | 0 | 0 | 5 | 0 | 0 | 5 | 0 | 0 | 4 | 0 | A | 4 | 0 | A | 5 | 0 | 0 | 5 | 0 | 0 |
| 34 | 5 | 0 | 0 | 5 | 0 | 0 | 4 | 0 | 0 | 5 | 0 | 0 | 5 | 0 | 0 | 5 | 0 | 0 | 4 | 0 | F | 4 | 0 | ABD | 5 | 0 | 0 | 5 | 0 | 0 |
| 35 | 5 | 0 | 0 | 4 | 0 | E | 5 | 0 | 0 | 5 | 0 | 0 | 4 | 0 | E | 5 | 0 | 0 | 3 | 0 | ABD | 4 | 0 | ABDI | 4 | 0 | E | 5 | 0 | 0 |
| 36 | 4 | 0 | 0 | 4 | 0 | E | 5 | 0 | 0 | 4 | 50 | L | 4 | 0 | E | 4 | 0 | 0 | 4 | 0 | BE | 4 | 0 | BDE | 4 | 0 | E | 4 | 0 | 0 |
| 37 | 5 | 0 | 0 | 5 | 0 | 0 | 4 | 0 | 0 | 5 | 0 | 0 | 5 | 0 | 0 | 5 | 0 | 0 | 4 | 0 | A | 5 | 0 | 0 | 5 | 0 | 0 | 5 | 0 | 0 |
| 38 | 4 | 0 | B | 4 | 0 | B | 4 | 0 | B | 5 | 0 | 0 | 5 | 0 | 0 | 5 | 0 | 0 | 4 | 0 | BD | 4 | 0 | BD | 4 | 0 | B | 5 | 0 | 0 |
| 39 | 4 | 0 | A | 5 | 0 | 0 | 4 | 0 | A | 5 | 0 | 0 | 5 | 0 | 0 | 5 | 0 | 0 | 4 | 0 | AD | 4 | 0 | D | 5 | 0 | 0 | 4 | 0 | A |
| 40 | 5 | 0 | 0 | 4 | 0 | B | 4 | 0 | 0 | 5 | 0 | 0 | 4 | 0 | 0 | 5 | 0 | 0 | 4 | 0 | BD | 4 | 0 | ABD | 4 | 0 | B | 5 | 0 | 0 |
| 41 | 4 | 0 | C | 3 | 0 | CE | 4 | 0 | C | 4 | 0 | C | 4 | 0 | C | 4 | 0 | C | 3 | 0 | BCDI | 3 | 0 | CDI | 3 | 10 | BCE | 4 | 0 | C |
| 42 | 4 | 0 | A | 4 | 0 | A | 4 | 0 | A | 4 | 0 | A | 5 | 0 | 0 | 4 | 0 | A | 4 | 0 | ADI | 5 | 0 | 0 | 4 | 0 | A | 4 | 0 | A |
| 43 | 5 | 0 | 0 | 5 | 0 | 0 | 5 | 0 | 0 | 4 | 0 | A | 4 | 0 | C | 4 | 70 | A | 5 | 0 | 0 | 4 | 0 | C | 5 | 0 | 0 | 5 | 0 | 0 |
| 44 | 5 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | 0 | 5 | 0 | 0 |
| 45 | 4 | 0 | A | 5 | 0 | 0 | 5 | 0 | 0 | 5 | 0 | 0 | 5 | 0 | 0 | 5 | 0 | 0 | 4 | 0 | A | 5 | 0 | 0 | 5 | 0 | 0 | 5 | 0 | 0 |
| 46 | 5 | 0 | 0 | 4 | 90 | BL | 4 | 0 | C | 4 | 30 | CL | 4 | 0 | C | 5 | 0 | 0 | 4 | 0 | C | 4 | 0 | BC | 4 | 20 | BC | 5 | 0 | 0 |
| 48 | | | | 100 | | 0 | 40 | | B1C | 70 | | B1C | 100 | | 0 | 30 | | C | 90 | | C4 | 70 | | B4C3H3D | 90 | | BC | 20 | | C |

TABLE II-continued

Postemergence Tests

| Example | Barngr V | Barngr K/F | Bindweed V | Bindweed K/F | Corn-F V | Corn-F K/F | Greenfox V | Greenfox K/F | Mrnglory V | Mrnglory K/F | Johngr V | Johngr K/F | Cotton/Lima Bean[1] V | Cotton/Lima Bean[1] K/F | Soybean V | Soybean K/F | Velvetlf V | Velvetlf K/F | Wheat V | Wheat K/F |
|---|---|---|---|---|---|---|---|---|---|---|---|---|---|---|---|---|---|---|---|---|
| 49 | 0 | 0 | 0 | 0 | 0 | 0 | 0 | 0 | 0 | 0 | 0 | 0 | 0 | 0 | 0 | 0 | 0 | 0 | 0 | 0 |
| 50 | 80 | A | 20 | B1E | 10 | AM | 0 | 0 | 30 | B2EA | 40 | AB1 | 70 | B2EAHE | 60 | B4A1EMP | 20 | B1E | 0 | 0 |
| 51 | 20 | AB1 | 10 | A | 20 | AB1 | 0 | 0 | 0 | 0 | 10 | A | 10 | A[1] | 10 | A | 0 | 0 | 0 | A |
| 54 | 10 | A | 0 | 0 | 0 | M | 0 | 0 | 10 | 0 | 10 | B1 | 10 | A[1] | | | 0 | 10 | 10 | AI |
| 55 | 10 | A | 10 | A | 10 | A | 0 | A | 0 | 0 | 10 | A | 10 | A[1] | 10 | AE | 10 | A | 0 | A |
| 57 | 20 | AB2EM | 80 | AB3 | 30 | AB2EM | 10 | 0 | 20 | AB4E | 20 | AM | 40 | AB2E[1] | 40 | AB3DE | 20 | AB3E | 10 | A |
| 58 | 60 | AB1 | 20 | B3E | 20 | AB1EM | 10 | A | 10 | B3E | 40 | AB2EM | 30 | AB2EM[1] | 20 | AB3DEIM | 10 | B3E | 10 | A |
| 59 | 0 | 0 | 0 | 0 | 10 | AM | 10 | A | 40 | AB1 | 40 | AB1 | 20 | AB1 | 30 | AB1 | 30 | AEI | 10 | 0 |
| 60 | 40 | B1C2 | 50 | B2C2 | 0 | B1C1E | 0 | 0 | 100 | C | 60 | B1C3 | 50 | B2H3[1] | 40 | B1C2DI | 60 | B1C3I | 10 | A |
| 61 | 0 | 0 | 0 | 0 | 0 | 0 | 0 | 0 | 0 | 0 | 0 | 0 | 0 | 0[1] | 0 | 0 | 0 | 0 | 0 | 0 |

FOOTNOTES
The footnotes in Table I are also applicable in Table II.

What is claimed is:

1. Plant growth and development modifying 2-(2-oxycarbonylcyclic)benzothiazoles of the formula

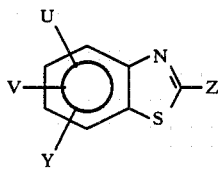

wherein
- U is selected from -hydrogen, -halogen, -lower alkyl, -lower haloalkyl, -lower alkoxy, -phenyl, and -phenoxy optionally carrying -halogen and -lower haloalkyl substituents;
- V is selected from -hydrogen and -halogen, or U and V taken together are —$C_4H_4$— joining adjacent ring positions;
- Y is selected from -hydrogen and -lower alkoxy;
- Z is selected from
  - (a) -phenyl, provided U, V and Y are not each -hydrogen; or
  - (b) -phenyl carrying 1 or 2 substituents independently selected from -halogen or two substituents taken together are —$C_4H_4$— joining adjacent ring positions; or
  - (c) a six-membered saturated or partially unsaturated carbocycle, optionally carrying a bicyclic —$CH_2$—bridge, and provided U is -hydrogen, -halogen or -phenyl and V and Y are -hydrogen; or
  - (d) a five or six-membered aromatic heterocycle containing 2 nitrogen atoms as the only hetero atoms, provided U is -hydrogen, -halogen or -phenyl and V and Y are -hydrogen; or
  - (e) a pyridine ring, provided U is -halogen or -phenyl and V and Y are -hydrogen; and Z also carries a 2-oxycarbonyl substituent of the formula

—COOW in which W is selected from -hydrogen, -lower alkyl, and an agriculturally acceptable cation.

2. Compounds of claim 1 wherein W is -hydrogen or an agriculturally acceptable cation.

3. Compounds of claim 1 wherein U is a 5- or 6-substituent selected from -halogen, -lower haloalkyl, -phenyl, and -phenoxy optionally carrying -halogen and -lower haloalkyl substituents.

4. Compounds of claim 1 wherein V and Y are -hydrogen.

5. Compounds of claim 1 wherein Z is selected from -phenyl or a pyridine ring.

6. A compound of claim 1 selected from 2-(2-carboxyphenyl)-5-phenylbenzothiazole, 2-(2-carboxyphenyl)-6-(2-chloro-4-trifluoromethylphenoxy)benzothiazole, 2-(2-carboxyphenyl)-5-(2-chloro-4-trifluoromethylphenoxy)benzothiazole, 2-(2-carboxyphenyl)-5-trifluoromethylbenzothiazole, 2-(2-carboxyphenyl)-6-phenylbenzothiazole, agriculturally acceptable cation salts of 2-(2-carboxyphenyl)-5-trifluoromethylbenzothiazole, 2-(2-carboxyphenyl)-6-phenoxybenzothiazole, 2-(2-carboxy-4-chlorophenyl)-6-phenylbenzothiazole, 2-(2-carboxy-5-chlorophenyl)-6-phenylbenzothiazole, 2-(2-carboxy-4-chlorophenyl)-6-phenoxybenzothiazole, 2-(2-carboxy-5-chlorophenyl)-6-phenoxybenzothiazole, 2-(2-carboxyphenyl)-5-phenoxybenzothiazole, and 2-(2-carboxy-6-pyridinyl)-5-phenylbenzothiazole.

7. 2-(2-Carboxyphenyl)-6-(2-chloro-4-trifluoromethylphenoxy)benzothiazole.

8. 2-(2-Carboxyphenyl)-5-phenylbenzothiazole.

9. 2-(2-Carboxyphenyl)-5-phenoxybenzothiazole.

10. 2-(2-Carboxy-6-pyridinyl)-5-phenylbenzothiazole.

11. Plant growth and development modifying compositions comprising in admixture with an agriculturally acceptable carrier a plant growth and development modifying effective amount of at least one 2-(2-oxycarbonylcyclic)benzothiazole of the formula

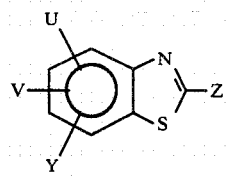

wherein
- U is selected from -hydrogen, -halogen, -lower alkyl, -lower haloalkyl, -lower alkoxy, -phenyl, and -phenoxy optionally carrying -halogen and -lower haloalkyl substituents;
- V is selected from -hydrogen and -halogen, or U and V taken together are —$C_4H_4$—joining adjacent ring positions;
- Y is selected from -hydrogen and -lower alkoxy;
- Z is selected from
  - (a) -phenyl optionally carrying 1 or 2 substituents independently selected from -halogen, -nitro, or two substituents taken together are —$C_4H_4$—joining adjacent ring positions; or
  - (b) a six-membered saturated or partially unsaturated carbocycle, optionally carrying a bicyclic —$CH_2$—bridge, and provided U is -hydrogen, -halogen or -phenyl and V and Y are -hydrogen; or
  - (c) a five or six-membered aromatic heterocycle containing 1 or 2 nitrogen atoms, as the only hetero atoms, provided U is -hydrogen, -halogen or -phenyl and V and Y are -hydrogen; and Z also carries a 2-oxycarbonyl substituent of the formula

—COOW in which W is selected from -hydrogen, -lower alkyl, and an agriculturally acceptable cation.

12. Compositions of claim 11 wherein said 2-(2-oxycarbonylcyclic)benzothiazole is selected from 2-(2-carboxyphenyl)-5-phenylbenzothiazole, 2-(2-carboxy-3-nitrophenyl)-5-chlorobenzothiazole, 2-(2-carboxyphenyl)-6-(2-chloro-4-trifluoromethylphenoxy)benzothiazole, 2-(2-carboxyphenyl)-5-(2-chloro-4-trifluoromethylphenoxy)benzothiazole, 2-(2-carboxyphenyl)-5-trifluoromethylbenzothiazole, 2-(2-carboxyphenyl)-6-phenylbenzothiazole, agriculturally acceptable cation salts of 2-(2-carboxyphenyl)-5-trifluoromethylbenzothiazole, 2-(2-carboxyphenyl)-6-phenoxybenzothiazole, 2-(2-carboxy-4-chlorophenyl)-6-phenylbenzothiazole, 2-(2-carboxy-5-chlorophenyl)-6-phenylbenzothiazole, 2-(2-carboxy-4-chlorophenyl)-6-phenoxybenzothiazole, 2-(2-carboxy-5-chlorophenyl)-6- phenoxybenzothiazole, 2-(2-carboxyphenyl)-5-phenoxybenzothiazole, and 2-(2-carboxy-6-pyridinyl)-5-phenylbenzothiazole.

13. Compositions of claim 11 wherein said 2-(2-oxycarbonylcyclic)benzothiazole is 2-(2-carboxyphenyl)-6-(2-chloro-4-trifluoromethylphenoxy)benzothiazole.

14. Compositions of claim 11 wherein said 2-(2-oxycarbonylcyclic)benzothiazole is 2-(2-carboxyphenyl)-5-phenylbenzothiazole.

15. Compositions of claim 11 wherein said 2-(2-oxycarbonylcyclic)benzothiazole is 2-(2-carboxyphenyl)-5-phenoxybenzothiazole.

16. Compositions of claim 11 wherein said 2-(2-oxycarbonylcyclic)benzothiazole is 2-(2-carboxy-6-pyridinyl)-5-phenylbenzothiazole.

17. A method of modifying the growth and development of plants which comprises applying to the locus where such modification is desired a plant growth and development modifying effective amount of at least one 2-(2-oxycarbonylcyclic)benzothiazole of the formula

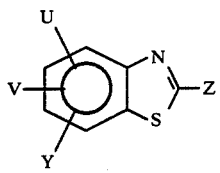

wherein
U is selected from -hydrogen, -halogen, -lower alkyl, -lower haloalkyl, -lower alkoxy, -phenyl, and -phenoxy optionally carrying -halogen and -lower haloalkyl substituents;
V is selected from -hydrogen and -halogen, or U and V taken together are —C4H4—joining adjacent ring positions;
Y is selected from -hydrogen and -lower alkoxy;
Z is selected from
(a) -phenyl optionally carrying 1 or 2 substituents independently selected from -halogen, -nitro, or two substituents taken together are —C4H4—joining adjacent ring positions; or
(b) a six-membered saturated or partially unsaturated carbocycle, optionally carrying a bicyclic —CH2—bridge, and provided U is -hydrogen, -halogen or -phenyl and V and Y are -hydrogen; or
(c) a five or six-membered aromatic heterocycle containing 1 or 2 nitrogen atoms, as the only hetero atoms, provided U is -hydrogen, -halogen or -phenyl and V and Y are -hydrogen; and
Z also carries a 2-oxycarbonyl substituent of the formula

COOW in which W is selected from -hydrogen, -lower alkyl, and an agriculturally acceptable cation.

18. A method according to claim 17 wherein said 2-(2-oxycarbonylcyclic)benzothiazole is selected from one 2-(2-carboxyphenyl)-5-phenylbenzothiazole, 2-(2-carboxy-3-nitrophenyl)-5-chlorobenzothiazole, 2-(2-carboxyphenyl)-6-(2-chloro-4-trifluoromethylphenoxy)benzothiazole, 2-(2-carboxyphenyl)-5-(2-chloro-4-trifluoromethylphenoxy)benzothiazole, 2-(2-carboxyphenyl)-5-trifluoromethylbenzothiazole, 2-(2-carboxyphenyl)-6-phenylbenzothiazole, agriculturally acceptable cation salts of 2-(2-carboxyphenyl)-5-trifluoromethylbenzothiazole,2-(2-carboxyphenyl)-6-phenoxybenzothiazole, 2-(2-carboxy-4-chlorophenyl)-6-phenylbenzothiazole, 2-(2-carboxy-5-chlorophenyl)-6-phenylbenzothiazole, 2-(2-carboxy-4-chlorophenyl)-6-phenoxybenzothiazole, 2-(2-carboxy-5-chlorophenyl)-6-phenoxybenzothiazole, 2-(2-carboxyphenyl)-5-phenoxybenzothiazole, and 2-(2-carboxy-6-pyridinyl)-5-phenylbenzothiazole.

19. A method according to claim 17 wherein said 2-(2-oxycarbonylcyclic)benzothiazole is 2-(2-carboxyphenyl)-6-(2-chloro-4-trifluoromethylphenoxy)benzothiazole.

20. A method according to claim 17 wherein said 2-(2-oxycarbonylcyclic)benzothiazole is 2-(2-carboxyphenyl)-5-phenylbenzothiazole.

21. A method according to claim 17 wherein said 2-(2-oxycarbonylcyclic)benzothiazole is 2-(2-carboxyphenyl)-5-phenoxybenzothiazole.

22. A method according to claim 17 wherein said 2-(2-oxycarbonylcyclic)benzothiazole is 2-(2-carboxy-6-pyridinyl)-5-phenylbenzothiazole.

23. A method of controlling the growth of plants which comprises applying to the locus where control is desired a herbicidally effective amount of at least one 2-(2-oxycarbonylcyclic)benzothiazole selected from 2-(2-carboxyphenyl)-5-phenylbenzothiazole, 2-(2-carboxy-3-nitrophenyl)-5-chlorobenzothiazole, 2-(2-carboxyphenyl)-6-(2-chloro-4-trifluoromethylphenoxy)benzothiazole, and 2-(2-carboxyphenyl)-5-(2-chloro-4-trifluoromethylphenoxy)benzothiazole.

24. A method according to claim 23 wherein said 2-(2-oxycarbonylcyclic)benzothiazole is 2-(2-carboxyphenyl)-6-(2-chloro-4-trifluoromethylphenoxy)benzothiazole.

25. A method of regulating the growth of plants which comprises applying to the locus where regulation is desired a plant growth regulant effective amount of at least one 2-(2-oxycarbonylcyclic)benzothiazole selected from 2-(2-carboxyphenyl)-5-phenylbenzothiazole, 2-(2-carboxyphenyl)-5-trifluoromethylbenzothiazole, 2-(2-carboxyphenyl)-6-phenylbenzothiazole, agriculturally acceptable cation salts of 2-(2-carboxyphenyl)-5-trifluoromethylbenzothiazole, 2-(2-carboxyphenyl)-6-(2-chloro-4-trifluoromethylphenoxy)benzothiazole, 2-(2-carboxyphenyl)-6-phenoxybenzothiazole, 2-(2-carboxy-4-chlorophenyl)-6-phenylbenzothiazole, 2-(2-carboxy-5-chlorophenyl)-6-phenylbenzothiazole, 2-(2-carboxy-4-chlorophenyl)-6-phenoxybenzothiazole, 2-(2-carboxy-5-chlorophenyl)-6-phenoxybenzothiazole, 2-(2-carboxyphenyl)-5-phenoxybenzothiazole, 2-(2-carboxy-6-pyridinyl)-5-phenylbenzothiazole, and 2-(2-carboxyphenyl)-5-(2-chloro-4-trifluoromethylphenoxy)benzothiazole.

26. A method according to claim 25 wherein said 2-(2-oxycarbonylcyclic)benzothiazole is selected from 2-(2-carboxyphenyl)-5-phenylbenzothiazole, 2-(2-carboxyphenyl)-5-phenoxybenzothiazole, and 2-(2-carboxy-6-pyridinyl)-5-phenylbenzothiazole.

27. A method according to claim 26 wherein said 2-(2-oxycarbonylcyclic)benzothiazole is 2-(2-carboxyphenyl)-5-phenylbenzothiazole.

* * * * *